United States Patent
Mohan et al.

(10) Patent No.: US 9,001,316 B2
(45) Date of Patent: Apr. 7, 2015

(54) USE OF AN OPTICAL SYSTEM SIMULATING BEHAVIOR OF HUMAN EYE TO GENERATE RETINAL IMAGES AND AN IMAGE QUALITY METRIC TO EVALUATE SAME

(71) Applicant: Bausch & Lomb Incorporated, Rochester, NY (US)

(72) Inventors: Nishant Mohan, Rochester, NY (US); Paul David Ludington, Brockport, NY (US); Ian G. Cox, Honeoye, NY (US); Amanda Kingston, Rochester, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 35 days.

(21) Appl. No.: 13/952,795

(22) Filed: Jul. 29, 2013

(65) Prior Publication Data

US 2013/0308094 A1    Nov. 21, 2013

(51) Int. Cl.
| | |
|---|---|
| G02C 7/02 | (2006.01) |
| G01B 9/00 | (2006.01) |
| A61B 3/00 | (2006.01) |
| G01M 11/02 | (2006.01) |
| A61B 3/032 | (2006.01) |

(52) U.S. Cl.
CPC .............. *A61B 3/0025* (2013.01); *G02C 7/027* (2013.01); *G01M 11/0264* (2013.01); *G01M 11/0257* (2013.01); *A61B 3/032* (2013.01)

(58) Field of Classification Search
CPC ........ G02C 7/024; G02C 7/027; G02C 7/028; A61B 3/0025; A61B 3/032; G01M 11/0235; G01M 11/0257; G01M 11/0264

USPC ............ 351/159.73, 159.74, 159.75; 356/125
See application file for complete search history.

(56) References Cited

U.S. PATENT DOCUMENTS

| | | | |
|---|---|---|---|
| 2002/0085172 A1 | 7/2002 | Altmann | |
| 2004/0246440 A1* | 12/2004 | Andino et al. | 351/177 |
| 2005/0254006 A1 | 11/2005 | Dai et al. | |
| 2009/0210054 A1* | 8/2009 | Weeber et al. | 623/6.11 |
| 2009/0281552 A1 | 11/2009 | Hiramatsu et al. | |
| 2013/0235340 A1* | 9/2013 | Dai et al. | 351/159.74 |
| 2014/0016091 A1* | 1/2014 | Dai | 351/205 |
| 2014/0125954 A1 | 5/2014 | Kingston et al. | |

FOREIGN PATENT DOCUMENTS

| | | |
|---|---|---|
| WO | 03/082162 A2 | 10/2003 |
| WO | 2009/152582 A1 | 12/2009 |

OTHER PUBLICATIONS

International Search Report and Written Opinion of the International Searching Authority mailed Oct. 17, 2014, in corresponding International Application No. PCT/US2014/048530 (13 pages).

* cited by examiner

*Primary Examiner* — Jordan Schwartz
(74) *Attorney, Agent, or Firm* — Toan P. Vo

(57) ABSTRACT

A method of predicting clinical performance of an ophthalmic optical correction using simulation by imaging a series of objects of different sizes by each of a plurality of eye optical systems, each of the eye optical systems including the ophthalmic optical correction, the method providing an output value representing the resolution and contrast performance of the optical design at that vergence for the eye optical systems.

14 Claims, 5 Drawing Sheets

USE OF AN OPTICAL SYSTEM SIMULATING BEHAVIOR OF HUMAN EYE TO GENERATE RETINAL IMAGES AND AN IMAGE QUALITY METRIC TO EVALUATE SAME

FIELD OF INVENTION

Whereas a previously filed application (unpublished) focused upon the use of computer assisted systems and methods for calculating visual performance of an ophthalmic optical correction, the present invention relates to use of an Optical Bench with Adaptive Optics systems and methods for predicting clinical visual performance of an ophthalmic optical correction. More particularly, the present invention relates to methods for predicting visual performance of an ophthalmic optical correction using simulation of an average person's imaging while wearing the ophthalmic optical correction by including the clinically measured optical aberrations, sans defocus, of a population of human eyes with an optical bench with adaptive optics to aid in the predictive analysis of a likely clinical performance of a particular lens design before conducting the actual patient based clinical trial of same lens design.

BACKGROUND OF THE INVENTION

Clinical studies of ophthalmic lenses and other ophthalmic corrections are expensive and time consuming endeavors. Numerous efforts have been made to calculate visual performance using computer simulation to supplement clinical studies, yet there remains a need for a more versatile and/or accurate method for predicting clinical visual performance of certain lens designs.

SUMMARY

Aspects of the present invention are directed to a method of predicting clinical performance of an ophthalmic optical correction using simulation by imaging a series of objects of different sizes by each of a plurality of eye optical systems. Each of the eye optical systems includes the ophthalmic optical correction. The present invention pertains to use of an optical system simulating behavior of human eye to generate retinal images and an image quality metric to evaluate these image. These, in conjunction, are used to predict actual patient based clinical performance of contact lens designs.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

The term "ophthalmic optical correction" refers to an ophthalmic lens used with an eye, an optical feature of an eye that has been refractively corrected or other ophthalmically modified features of an eye optical system. For example, an optical feature of an eye that has been refractively corrected may include a crystalline lens or cornea that has been reshaped or otherwise optically modified using a mechanical or optical technique (e.g., LASIK or change of index of refraction).

The term "ophthalmic lens" refers to any artificial lens for use with an eye (e.g., a spectacle, a contact lens, an intraocular lens, a corneal inlay or a corneal onlay). An ophthalmic lens may comprise one or more optical elements. An ophthalmic lens may be multifocal or single vision. An ophthalmic lens may be refractive and/or diffractive. An ophthalmic lens may be monofocal or multifocal (e.g., bifocal or trifocal).

The term "population of eye optical systems" is used herein to refer to a plurality of optical systems, each optical system including the optical portion of an eye.

Figure 4:
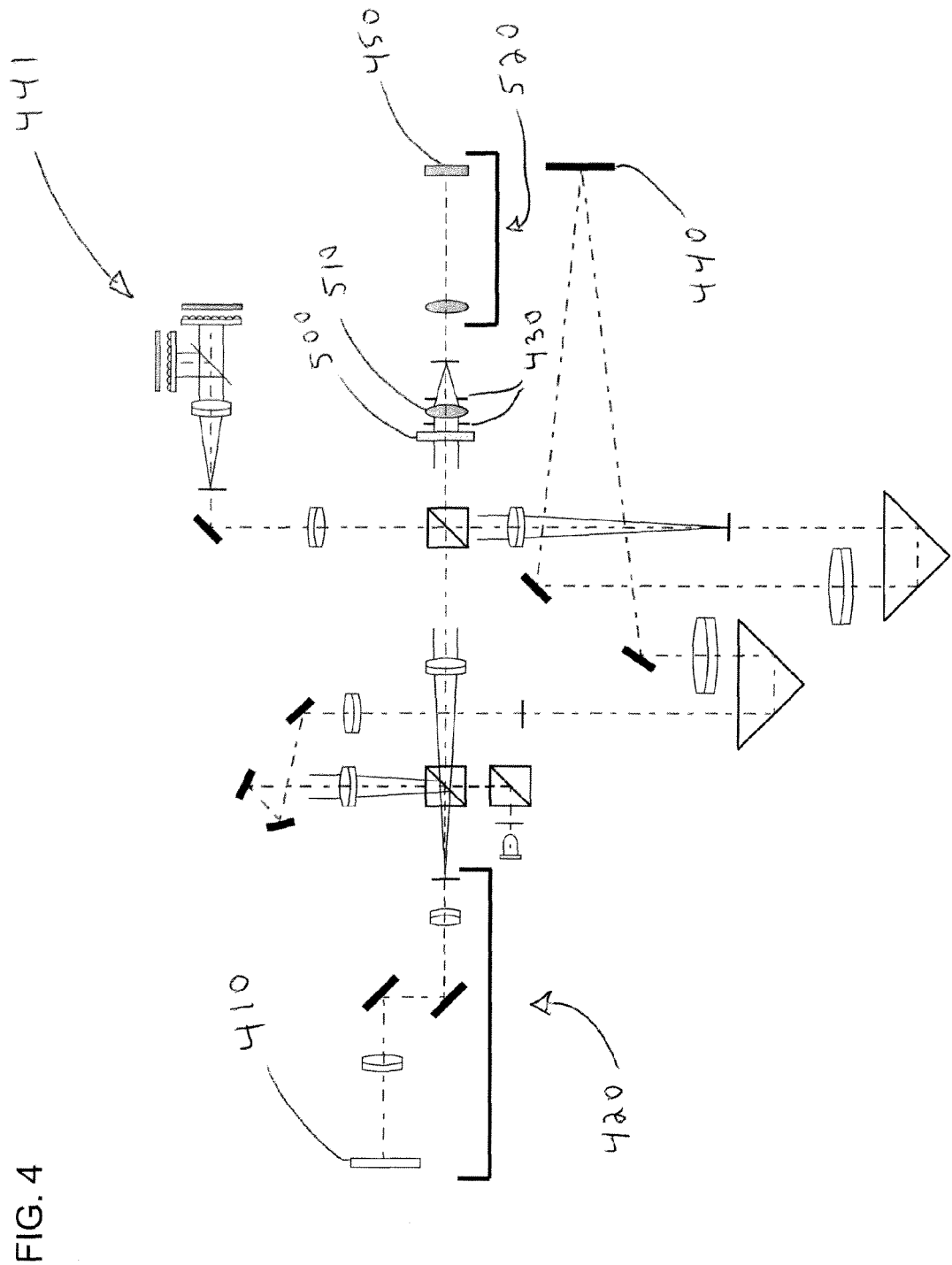
FIG. 4 is a schematic of an adaptive optics bench.

Referring now to FIG. 4, an adaptive optics multifocal bench is used to test a contact lens or intraocular lens optical design through focus and represent a patient's predicted visual outcome. A test target 410 will be viewed at optical vergences representing beyond infinity, infinity, and then from distance through near similar to the viewing distances that a patient might typically experience (e.g., distance through 4.00 D in 0.125 D steps). The contact lens or intraocular lens optical design will be represented by a zero defocus rigid PMMA optic 500 mounted in the system. Optionally, the rigid PMMA optic 500 may be replaced by a soft-contact lens conformed on a model cornea (not shown) to simulate the behavior resulting from conformation of the lens on the human eye in presence of inherent aberrations. The individual patient ocular optical errors, other than defocus, will be represented by a series of Zernike co-efficients representing that patient's ocular wavefront sans defocus (hereinafter, ocular wavefront). This ocular wavefront can be measured clinically using a wavefront sensor designed for clinical measurements (e.g., B+L Zywave, AMO COAS). The pupil size can be measured as part of the wavefront measurement procedure. When desirable, evaluation of the change in performance of a particular lens design with changing pupil size in presence of human aberrations can be achieved by generating multiple and scoring same for different pupil sizes. This embodiment of the invention herein allows for simulating and quantifying the performance of a particular lens design for different pupil sizes.

When desirable, the contact lens design or a conformed soft lens can be decentered with respect to optical axis. This allows for simulation of the performance of the lens in case of de-centration on the eye.

This individual patient ocular wavefront can then be implemented using the deformable mirror in an adaptive optics multifocal bench, by implementing the patient's Zernike co-efficients to represent the wavefront error and repeating same for a population of patients to the pathway between the object target and the design optic. By measuring a cohort of individual eyes, a predictive representation of the performance of the optical design across a population sample of subjects can be generated. This data set can be thought of as a "virtual clinical" study prior to actual contact lens or intraocular lenses being made with the desired optical design and tested in the traditional clinical fashion. The invention as described herein allows assessment of more optical designs in the early stage of development, ensuring that the design(s) that go to a traditional clinical study have the greatest chance of being successful.

The steps required to perform a measurement (for providing output data) representing a single patient (assuming the system is validated and calibrated) is as follows:

mounting the ophthalmic optical correction 500 in front of a model eye 510, adjusting a model eye pupil size 430 to represent an actual pupil size of a patient measured at the recording of an ocular wavefront sans defocus and pupil size of the patient, adjusting the deformable mirror 440 using the ocular wavefront sans defocus as an input 441 to represent the wavefront error of the patient eye, moving an object target 410 to beyond optical infinity and capturing an image 520 of the object target 410, moving the object target 410 to a vergence more positive by a known distance and capturing a second image 520 of the object target 410, continuing to move the object target 410 to a more positive vergence in steps by a known distance until a determined total vergence is reached while generating a series of letters having different letter sizes at each object target 410 distance, capturing an image 520 at all known distance step locations and all different letter sizes at each object target 410 distance, subjecting each captured image 520 at all known distance step locations to an algorithm to provide an output value representing the resolution and contrast performance of the optical design 500 at that vergence for the eye optical systems, comparing the output value at each vergence to a threshold to determine a just discernible object size for the given eye optical system at that vergence, and repeating the above method steps for any number of individual patients representing a predefined population sample.

Further embodiments of the invention disclosed herein include one or more of the following steps:
1) Mounting the rigid contact lens or intraocular lens optical design in front of the model eye.
2) Adjusting the model eye pupil size to represent the actual pupil size of the patient measured at the time of recording the ocular wavefront.
3) Adjusting the deformable mirror using Zernike co-efficients as the input to represent the wavefront error of a patient eye to be tested.
4) Moving the object target to beyond optical infinity (usually −1.00 D) and capture an image of the object target.
5) Moving the object target to a vergence more positive by 0.125 D and capture a second image.
6) Continuing to move the object target to a positive vergence in 0.125 D steps until a total vergence of (typically) +4.00 D positive vergence, capturing an image at all step locations.
7) Capturing each image and then subjecting same to an algorithm designed to provide an output metric representing the resolution and contrast performance of the optical design at that vergence for the individual patient's eye. This metric can be a clinically based metric such as log MAR acuity, or an optical based metric such as Strehl Ratio etc.
8) The method of the invention disclosed herein may be repeated for any number of individual patients representing a predefined population sample (e.g., presbyopic, pre-presbyopic, aphakic, pseudopakic).
9) The performance metrics for all patients are graphed vs. vergence for final evaluation, either individually or as a population mean.

Even further embodiments of the invention disclosed herein include:
10) Apparatus (adaptive optics bench) and method for evaluating performance of contact lens designs while accounting for aberrations in eye. The apparatus facilitates:
    simulation of target objects of variable size as in a clinical setting,
    change in location of the simulated object with respect to the eye,
    simulation of changing pupil size of human eye for each object location,
    introduction of aberrations present in the human eye into the optical system,
    capture of image of a size expected on the retina.
11) The system employs image quality assessment to score the representative retinal images in a manner which can provide a predicted visual acuity value, similar to that produced in a clinical study with real patients. In use, the system will be setup with pupil size and aberrations that represent an individual patient eye and the design to be tested will be measured on that eye for all object distances to generate through focus images of the performance of that lens design. Pupil size and aberration parameters for a second eye will be input to the system and the images through focus repeated. This process will be repeated for a number of patients' individual eye parameters 925 for instance) and the results generated from the image metrics will be statistically treated in the same way individual results from a clinical study would be analyzed. With this system we will be running a "virtual clinical".
12) Evaluating performance of multifocal contact lens designs at different target object locations: The apparatus and method of claim 1 wherein the position of target object is changed and image scores are generated for different locations of the lens in presence of human aberrations. The performance of the multi-focal design is evaluated based on consistency of performance across different object locations.
13) Evaluating performance of a conformed lens in presence of human aberrations: The apparatus of embodiment 1 wherein the contact lens design on the solid substrate has been replaced by soft-contact lens conformed on a model cornea to simulate the behavior resulting from conformation of the lens on the human eye in presence of inherent aberrations.
14) Evaluating performance of a decentered lens in presence of human aberrations: The apparatus of embodiment 1 wherein the contact lens design or a conformed soft lens is decentered with respect to optical axis. This simulates performance of the lens in case of de-centration on the eye.
15) Evaluating change in retinal image formation with contact lenses with human aberrations: The apparatus and method of embodiment 1 wherein scoring of images has been replaced by capture of individual retinal images. Providing clinical understanding of retinal image in real human eye.
16) Evaluating change in performance of lens design with changing pupil size in presence of human aberrations: The apparatus and methods of embodiment 1 wherein multiple images are generated and scored for different pupil sizes. Simulating and quantifying the performance of the design for different pupil sizes.
17) Evaluating retinal image of natural scene in presence of human aberrations: The apparatus and method of embodiment 1 wherein target objects are switched from characters in the clinic to natural scenes encountered in real life. Simulating qualitative performance of the lens design under different scenarios.

18) Evaluating performance in different contrast conditions: The apparatus and method of embodiment 1 wherein target objects are varied not only in size but also contrast, described as variation in brightness between background and object of interest. Simulating quantitative performance of the lens design in presence of difference contrast conditions.

19) Simulating patient specific situations and evaluating lens design: The apparatus and method of embodiment 1 wherein the system parameters are modified to simulate situations where both environmental and patient related parameters. For instance, simulating night vision driving performance by using low contrast green and white targets with large pupil setting.

Aspects of the present invention are directed towards attaining a prediction of clinical visual performance of an ophthalmic optical correction by simulation through use of the ophthalmic optical correction in a population of eye optical systems with which the correction is to be used. It should be understood that an eye optical system generates a retinal image.

Figure 1:
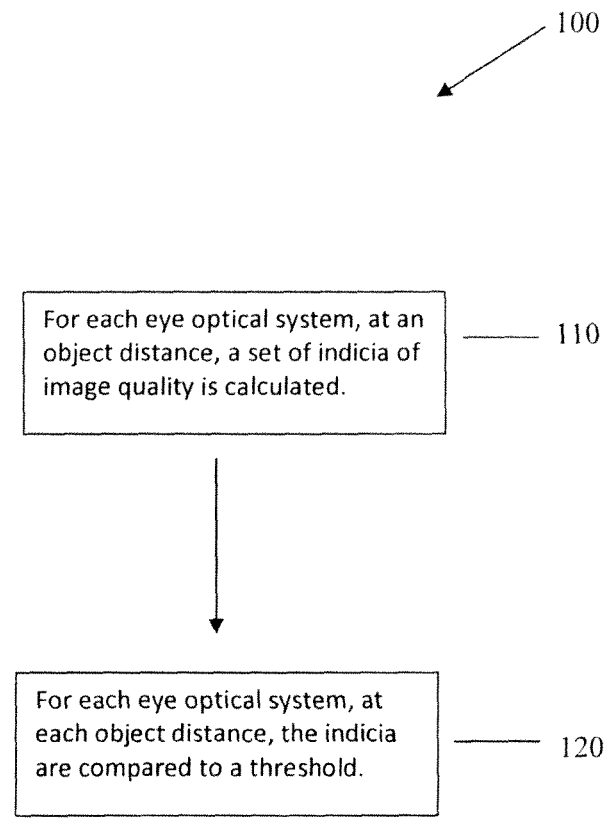
FIG. 1 is a flow chart showing an example of a method of calculating clinical performance of a ophthalmic optical correction according to aspects of the present invention.

An aspect of the invention is directed to a method of calculating clinical performance of an ophthalmic optical correction using simulation on an optical bench with adaptive optics by imaging a series of objects of different sizes by each of a plurality of eye optical systems, each of the eye optical systems including the ophthalmic optical correction. FIG. 1 is a flow chart showing an example of such a method 100. An eye optical system including the ophthalmic optical correction is also referred to herein as a modified eye optical system.

The ophthalmic optical correction is located in each optical system in a manner consistent with the anticipated use. For example, a contact lens is located in contact with the outer surface of the cornea of the eye, an intraocular lens is located in the eye at an appropriate location with the eye's natural lens being omitted or remaining in place, and/or a cornea is appropriately modified to correspond to a refractive procedure.

Figure 5:
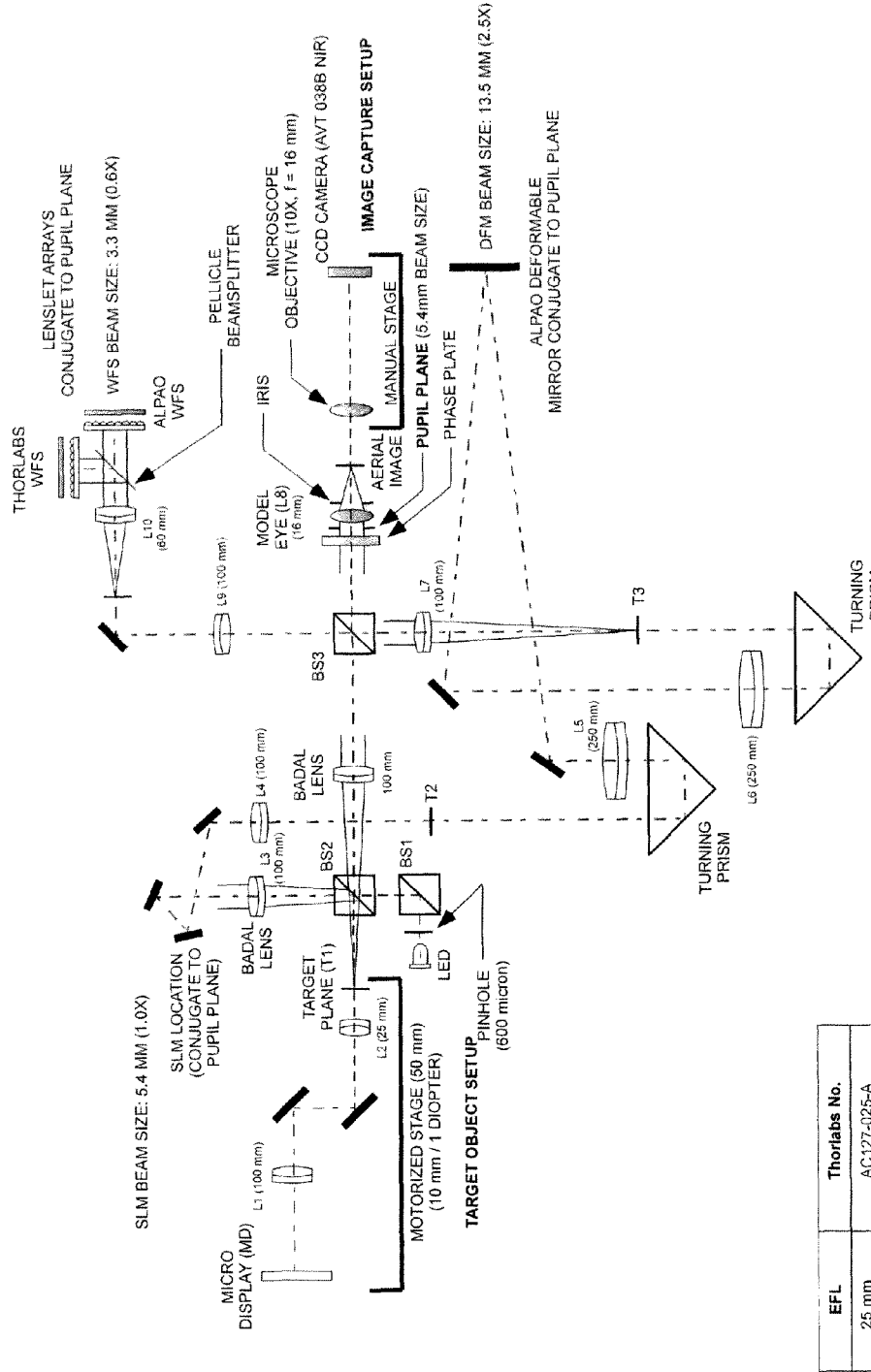
FIG. 5 is a detailed image of the bench of FIG. 4 identifying certain specific optical elements and commercial source for same. It is to be understood that one of ordinary skill in the art to which this invention applies would be able to read and understand FIG. 5 without need for further elaboration.

Simulation of imaging by an eye can be achieved using any suitable technique. For example, optical and anatomical parameters can be entered into an optical design software system (e.g., Zemax. Code V or Oslo) to produce an eye model corresponding to a modified eye optical system. Simulated imaging may be achieved, for example, (1) by tracing rays from a given object through the eye model and/or (2) by obtaining a point spread function for the model and convolving the point spread function with the object. Simulated imaging may he achieved, for example, through use of an optical bench having adaptive optics, for example as is shown in FIG. 5. The simulated imaging results in the generation of a modified eye optical system output (e.g., a retinal image). Simulated imaging may be repeated for each object size or for a subset of the series of objects. The sizes of the objects of different sizes may correspond to typical logMAR or Snellen eye chart sizes or using any other suitable selection technique. The inventors have found that a series of a same letter of different sizes is effective (e.g., a series of O's, E's or X's). However, as set forth above, certain embodiments will allow for evaluating retinal image of natural scene in presence of human aberrations wherein target objects are switched from characters in the clinic to natural scenes encountered in real life. Simulating the qualitative performance of the lens design under different scenarios. Evaluating performance in different contrast conditions wherein target objects are varied not only in size but also contrast, described as variation in brightness between background and object of interest. Simulating the quantitative performance of the lens design in the presence of difference contrast conditions. Moreover certain embodiments will allow for simulating patient specific situations and evaluating lens design wherein the system parameters are modified to simulate situations where both environmental and patient related parameters. For example, simulation of night vision driving performance by using low contrast green and white targets with large pupil setting.

Each object in the series (i.e., the series of objects of different sizes) may be imaged at each of a plurality of object distances. At one or more of the distances, a subset of the series of objects in the series may be imaged. Object distances may range from near distance (e.g., 4 diopters (i.e., 25 cm) to a far distance of infinity) or a subset thereof. In some instances, an ophthalmic optical correction may be evaluated at a single distance, most commonly the far distance (i.e., effectively an infinite object distance). A technique using only the far distance is most commonly used with ophthalmic optical corrections to be used by non-presbyopic individuals.

For example, for each eye, the following optical and anatomical parameters may be determined or measured to produce the eye model: ocular aberrations, pupil diameter, corneal curvature, corneal thickness, anterior chamber depth and axial length. For any parameters that vary as a function of object location (e.g., ocular aberrations, pupil diameter), a value may be measured for each object distance and used to calculate the indicia of image quality set forth below.

To determine visual performance, for each eye optical system, at an object distance, a set of indicia of image quality is calculated (step 110). Each indicium of the set of indicia corresponds to a different object in the series of objects and is indicative of the image quality when the object is imaged by the eye optical system onto a retina. Image quality can comprise a measure of resolution and/or contrast. For example, a resolution indicium can be calculated using a cross-correlation algorithm of the output image of the modified eye optical system with a perfect representation of the object at he proper magnification letter. Other image quality metrics may include measures of resolution and/or contrast such as modulation transfer function (MTF) (where low frequencies are generally associated with a measure of contrast and high frequencies are generally associated with a measure of resolution), Strehl ratio, visual Strehl optical transfer function (VSOTF) or a combination of these indicia of image quality. As stated above, at each distance (e.g., at 9 distances), an indicia is calculated for each object in the series of objects of different sizes or for a subset of objects in the series. Also, as stated above, for a given eye, different anatomical parameters may be used to calculate indicia at different object distances.

For each modified eye optical system, at each object distance, the indicia are compared to a threshold to determine a just-discernible object size (step 120). Calculation of a threshold is discussed in greater detail below. The smallest object that results in an indicium greater than the threshold is the just-discernible object size.

Figure 2:
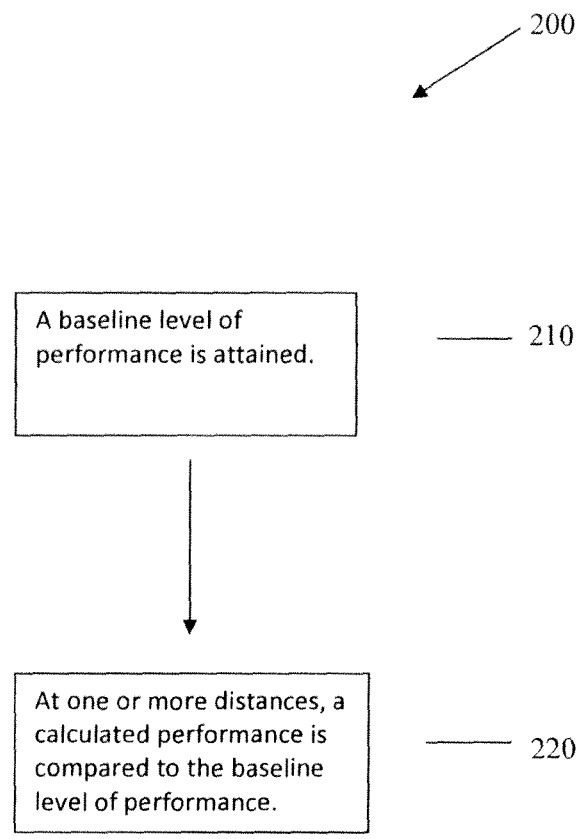
FIG. 2 is a flow chart showing another example of a method that includes further steps that may be used to calculate visual performance of an ophthalmic optical correction according to aspects of the present invention.

To further determine a visual performance of an ophthalmic optical correction, a baseline level of performance may be attained. FIG. 2 is a flow chart showing a method 200 including further steps that may be used to determine visual performance. At step 210, the baseline level of performance may be attained by (1) calculating or clinically measuring a performance of a baseline eye optical system that includes a baseline ophthalmic optical correction (i.e., any ophthalmic optical correction that is different than the ophthalmic optical correction) or (2) calculating or clinically measuring a performance of a baseline eye system without an ophthalmic optical correction. For the baseline eye optical system, an indicia of image quality is calculated or measured at each distance (e.g., 9 distances) for the plurality of objects of different sizes to determine the object size that is just discernible (i.e., having an image metric at or greater than the threshold).

At step 220, one or more distances, the calculated performance of the ophthalmic optical correction in an eye system is compared to performance of the baseline ophthalmic optical correction in an eye system in the following manner. From (1) the performance results for the baseline eye optical system, (2) the calculated results for the modified eye optical system including the ophthalmic optical correction under test, and (3) a given set of objective criteria, it is possible to establish a measure of how well the modified eye optical system that includes the ophthalmic optical correction under test performed as compared to the baseline eye system. For example, by comparing the results for the ophthalmic optical correction under test and the baseline ophthalmic optical correction, it can be determined what percentage of wearers would prefer the ophthalmic optical correction under test based on the set of criteria (e.g., for a percentage of wearers the correction is better at a given distance or achieves better performance based on a weighted measure of several distances).

The criteria can include a comparison of the modified eye system and the baseline eye system using values from individual eye systems or averages across a population. The criteria, also, may include values from individual distances or use an average performance at two or more distances, with different distances having the same or different weightings. It will be appreciated that performance at the far distance is usually given the greatest weighting. Criteria may include only individual values or only averages, or any combination thereof.

After performing the above method steps and/or calculations to determine performance, the ophthalmic optical correction under test may be modified (or another ophthalmic optical correction may be modified) based on determined performance to include or omit features of the ophthalmic optical correction. For example, modification can be performed if the calculated performance has a selected value (e.g., above, below or at a selected threshold). For example, features of a lens can be implemented into a lens design after determining that the performance was adequate or determining that the calculated performance was superior to the baseline lens.

Also, after performing the above method steps and/or calculations to determine performance, it is possible to compare the predicted clinical performance of the ophthalmic optical correction under test to a clinical performance (calculated or clinically measured) of a second ophthalmic optical correction and to select the first ophthalmic optical correction for use or the second ophthalmic optical correction. For example, the selection can be made depending on their relative performances.

Also, if performance of only a single ophthalmic optical correction is predictively determined, the ophthalmic optical correction may be selected for use based on the predictively determined performance if the indication of clinical performance meets selected criteria (e.g., performance was above, below or at a selected threshold).

As discussed above and shown in FIGS. 4 and 5, simulation of imaging by a population of eyes can be achieved by various techniques. An alternative technique to computer simulation using a software system is the use of an adaptive optic system to simulate the performance of the eyes including an ophthalmic optical correction. The adaptive portion of the optic system 440 may include means such as MEMS, voice coil, silicon light modulator, liquid crystal component that is refractive or reflective to simulate aberrations of the eye. The optic system may include a pupil having a variable aperture 430. A simulated retinal image 450 for a simulated eye optical system including the ophthalmic optical correction (phase plate) 500, pupil plane, model eye, aerial image manual stage, and microscope objective can be captured from the adaptive optical system on an opto-electronic transducer such as a CCD 450. The images captured and subsequent processing of the images is the same as described above.

Calculation of Threshold

Figure 3:
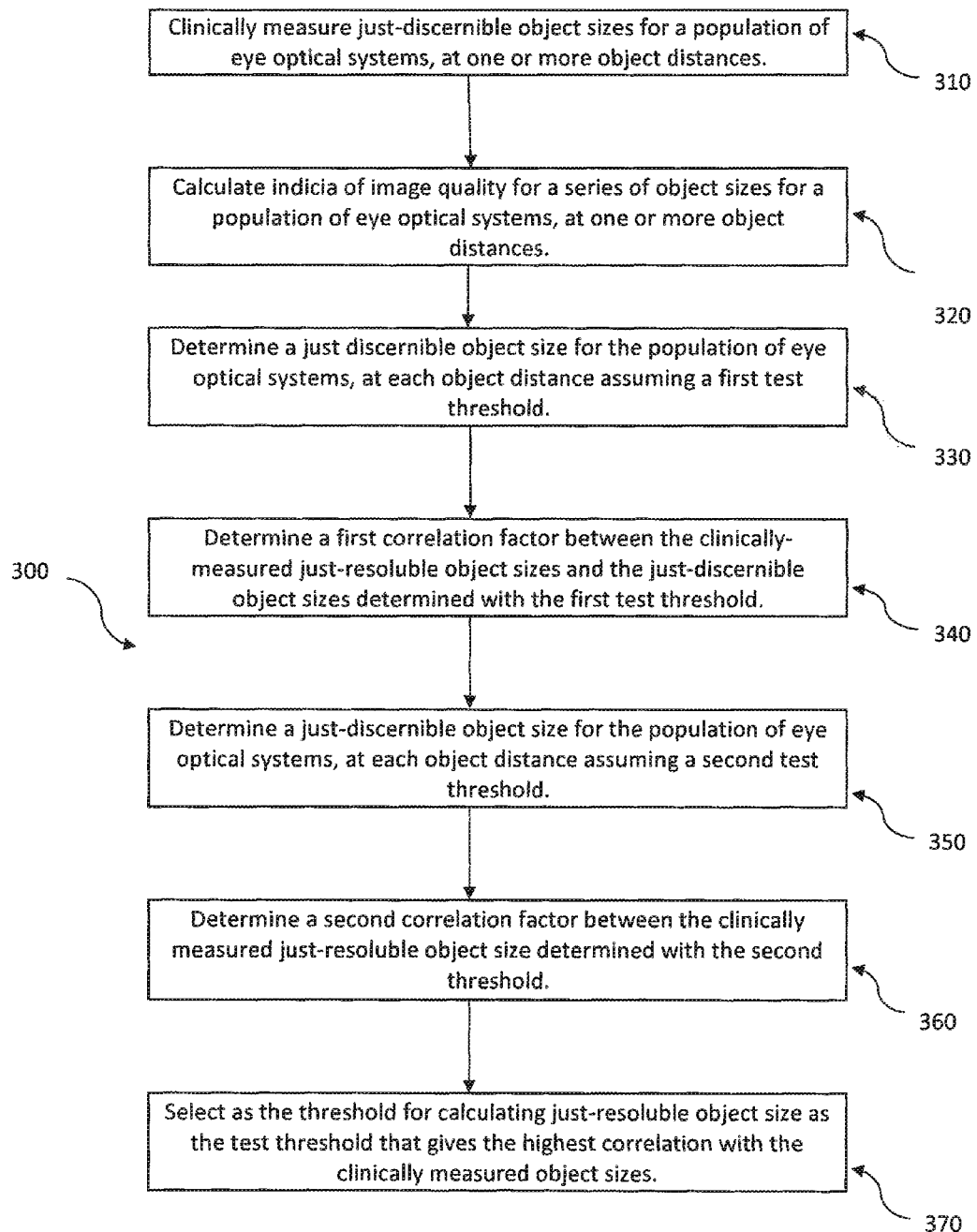
FIG. 3 is a flow chart showing an example of a technique for establishing a threshold value according to aspects of the present invention.

As set forth above, a calculated level of performance at a particular distance, for a modified eye system, can be determined by comparing the calculated indicia of image quality to a threshold and taking as the just-resolvable object size the smallest object size that has a calculated indicia of image quality that is greater than the threshold. An example of a technique for establishing a threshold value is set forth below (FIG. 3); however, any suitable technique can be used.

Firstly, it should be appreciated that, by establishing an appropriate threshold, a relationship between the calculated results and the actual, clinical performance can be established.

To determine a threshold, a population of eye optical systems (e.g., 90 patients, N=180 eyes) is assembled. Ideally the patients' eyes are representative of the population of patients/consumers who are intended to wear the ophthalmic lens and can include sub-populations of patients, each sub-population including a selected number of patients with a given characteristic or condition. For example, a selected number can be advanced presbyopes, a selected number can be early presbyopes, and a selected number could be non-presbyopes.

A subjective, clinical measure of visual acuity is measured at one or more object distances for each eye optical system. For example, a logMAR or a Snellen chart is used in a conventional manner (i.e., using a series of objects of different sizes) to obtain a smallest resolved object size (step 310). A chart for clinical use may include a series of a same letter of different sizes. Accordingly, if nine object distances are used, each eye has associated with it nine logMAR or Snellen values. The collection of clinically measured, just-discernible object sizes is referred to herein as a clinical series of data.

Also, during the subjective, clinical measurements, for each eye, optical and anatomical parameters, as set forth above, are measured. The anatomical parameters may include any appropriate anatomical data to account for variations of the optical and anatomical parameters as a function of object distance. For ocular aberrations measurements, it is typically advantageous if they are measured while the patient fixates on the smallest resolvable object at a particular object distance. The parameters are used to produce eye models corresponding to each eye in the population by entering optical and anatomical parameters into an optical design software system (e.g., Zemax, Code V) or using an optical bench with adaptive optics as set forth above. Eyes included in the population (N) may be aided by a lens (i.e., a lens in addition to the ophthalmic optical correction under test) or not, provided that any such aid is included in the model the eye. A simulated population of eyes is thereby generated.

After entering the data, for each eye, at each distance, a simulated series of object sizes is input into an eye model, the simulated series being a representation of the series of objects used in the subjective, clinical test. For each eye, and at each distance, an indicium of image quality is calculated for each object size (or a suitable subset of object sizes) (step 320).

Calculated performance for each eye is determined by assuming a first, test threshold value for the just-resolvable object size for each eye at each distance (step 330). The clinical results for each eye at all object distances, results in a series of just-resolvable object sizes. The resulting just-resolvable object sizes for all eyes and all distance are compared to the subjective, clinical results. A correlation factor is determined for the first, test threshold (step 340). For example, the correlation is determined by assuming a linear relationship between the data.

Next, calculated outputs for each eye are determined by assuming a second test threshold value for determining the just-resolvable object size (step 350). The resulting object sizes for all eyes and all distances are compared to the subjective, clinical results. A correlation factor is determined for the second, test threshold (step 360). The process is repeated for any number of additional thresholds.

The appropriate threshold is selected as the test threshold that gives the highest correlation between the calculated and subjective, clinically-observed just-resolved object sizes (step 370).

It will be appreciated that the selected linear relationship may not extend through the data such that a given calculated just-resolvable object size (e.g., 0.2 logMAR) corresponds to a calculated object size (0.2 logMAR). In fact, the inventors have determined that the relationship between the calculated just-resolvable and clinically observed just-resolvable object size is typically non-linear (e.g., a polynomial or other fitting curve provides a better correlation). The non-linear fitting curve compensates for the fact that, independent of object distance, patient visual performance is typically better than expected (i.e., better than calculations would indicate) for larger letters and worse than expected for smaller letters.

It will be appreciated that once the correction between calculated just-resolvable object sizes and clinically-observed just-resolvable object sizes is determined, it is possible to convert (i.e., map) a subsequently calculated just-resolvable object sizes for any ophthalmic optical correction to anticipated clinical just-resolvable object sizes for any or all eye optical systems in the population.

Additional Techniques for Calculating Indicia of Image Quality

It will be appreciated that the accuracy of the calculated just-resolvable object size could be improved if it were possible to improve the correlation between calculated just-resolvable object size and the clinically-observed just-resolvable object size. To this end the inventors have determined that, in some instances, it is desirable to avoid a situation in which a disproportionate amount of information about contrast or resolution is included in an indicium or set of indicia. Accordingly, at each distance, for each object size, aspects of the present invention include, calculating a given indicium of image quality by combining two or more image quality metrics, at least one of said metrics providing a greater amount of (or substantially only) information about contrast of a retinal image and another providing a greater amount of (or substantially only) information about resolution of a retinal image, to obtain an indicium of image quality. The step of combining may be repeated for each object size at a given distance or only the object size that is just-resolvable. It will be appreciated that an appropriate amount of resolution and contrast is determined by further including an amount resolution information or contrast information and determining if the correlation between calculated results and clinical results is increased or decreased. Typically, the combining is achieved by multiplying the indicia including greater amount resolution information and the indicia including greater amount contrast information; however, other combinations may be used such as addition with or without a weighting factor.

For example, in some embodiments, for each of the objects in the series, an indicia containing substantially only resolution information is calculated for each eye output (i.e., retinal image), for example, using a cross-correlation technique as set forth above; and for each of the objects in the series, an indicia containing substantially only contrast information is calculated for each eye output. The two indicia containing substantially only resolution information is combined with the indicia containing substantially only contrast information to form the indicia of image quality.

The indicia containing substantially only contrast may be any suitable measure of contrast indicative of the image contrast when the object is imaged by the optical system. Image contrast can be calculated in many ways, for example, by calculating a peak intensity level in a light region of the object image and a minimum intensity level in a dark region of the object image and using the following equation $$\text{Contrast} = \frac{\text{Intensity}_{max} - \text{Intensity}_{min}}{\text{Intensity}_{max} + \text{Intensity}_{min}}$$

where Intensity$_{max}$ and Intensity$_{min}$ are indications (e.g., electronic detector output) of signal strength in a region of maximum intensity in the image and in a region of minimum intensity in the image, respectively. For example, signal strength may be measured as a number of rays to hit specific areas in the image.

It will be appreciated that an indicium of image quality including two or more metrics can be used for calculation of the threshold (as set forth above) and for calculation of lens performance (as set forth above).

The critical aspects of an apparatus such as an adaptive optics bench for use in the inventive method described herein for evaluating performance of contact lens designs while accounting for aberrations in eye are set forth in FIG. 4 wherein means for simulation of target objects of variable size as in a clinical setting (410), means for change in location of the simulated object with respect to the eye (420), means for simulation of changing pupil size of human eye for each object location (430), means for introduction of aberrations present in the human eye into the optical system (440, 441), and means for capture of image of a size expected on the retina (450).

The adaptive optics bench optical layout as shown in FIGS. 4 and 5 and described herein as a system (the system) employs image quality assessment to score the representative retinal images in a manner which can provide a predicted visual acuity value, similar to that produced in a clinical study with real patients. In use, the system will be setup with pupil size and aberrations that represent an individual patient eye and the design to be tested will be measured on that eye for all object distances to generate through focus images of the performance of that lens design. Pupil size and aberration parameters for a second eye will be input to the system and the images through focus repeated. This process will he repeated for a number of patients individual eye (N) parameters (N=925 for instance) and the results generated from the image metrics will be statistically treated in the same way individual results from a clinical study would be analyzed. With this system we will be running a "virtual clinical study".

The method comprises mounting the ophthalmic optical correction 500 in front of a model eye 510, adjusting a model eye pupil size 430 to represent an actual pupil size of a patient measured at the recording of an ocular wavefront sans defocus and pupil size of the patient, adjusting the deformable mirror 440 using the ocular wavefront sans defocus as an input 441 to represent the wavefront error of the patient eye, moving an object target 410 to beyond optical infinity and capturing an image 520 of the object target 410, moving the object target 410 to a vergence more positive by a known distance and capturing a second image 520 of the object target 410, continuing to move the object target 410 to a more positive vergence in steps by a known distance until a determined total vergence is reached while generating a series of letters having different letter sizes at each object target 410 distance, capturing an image 520 at all known distance step locations and all different letter sizes at each object target 410 distance, subjecting each captured image 520 at all known distance step locations to an algorithm to provide an output value representing the resolution and contrast performance of the optical design 500 at that vergence for the eye optical systems, comparing the output value at each vergence to a threshold to determine a just discernible object size for the given eye optical system at that vergence, and repeating the above method steps for any number of individual patient eyes representing a predefined population sample.

In some embodiments, the ophthalmic optical correction comprises use of an ophthalmic lens.

The set of indicia of image quality may comprise an indication of resolution. In some embodiments, the set of indicia of image quality comprises substantially only resolution information.

The set of indicia of image quality may comprise an indication of contrast. In some embodiments, the set of indicia of image quality comprises substantially only contrast information.

In some embodiments, the set of indicia of image quality comprises resolution information and contrast information.

In some embodiments, the step of calculating a set of indicia of image quality comprises, for at least one of the plurality of object distances, calculating indicia of image quality for only a subset of the series of objects of different sizes.

In some embodiments, the step of calculating a set of indicia of image quality comprises, for at least one of the eye optical systems, calculating using different anatomical parameters for objects at different distances of the plurality of object distances.

The series of objects of different sizes may consist of a series of same letters of different sizes.

The method may comprise calculating the set of indicia of image quality at only one object distance for each eye optical system.

Certain preferred embodiments of the invention described herein would include:

1. A method of predicting clinical performance of an ophthalmic optical correction by imaging on an optical bench having an adaptive optics system comprising a deformable mirror and a wavefront sensor a series of objects of different sizes by each of a plurality of an eye optical system, each of the eye optical systems including the ophthalmic optical correction, the method comprising:
   mounting the ophthalmic optical correction 500 in front of a model eye 510,
   adjusting a model eye pupil size 430 to represent an actual pupil size of a patient measured at the recording of an ocular wavefront sans defocus and pupil size of the patient,
   adjusting the deformable mirror 440 using the ocular wavefront sans defocus as an input 441 to represent the wavefront error of the patient eye,
   moving an object target 410 to beyond optical infinity and capturing an image 520 of the object target 410,
   moving the object target 410 to a vergence more positive by a known distance and capturing a second image 520 of the object target 410,
   continuing to move the object target 410 to a more positive vergence in steps by a known distance until a determined total vergence is reached while generating a series of letters having different letter sizes at each object target 410 distance,
   capturing an image 520 at all known distance step locations and all different letter sizes at each object target 410 distance,
   subjecting each captured image 520 at all known distance step locations to an algorithm to provide an output value representing the resolution and contrast performance of the optical design 500 at that vergence for the eye optical systems,
   comparing the output value at each vergence to a threshold to determine a just discernible object size for the given eye optical system at that vergence, and
   repeating the above method steps for any number of individual patients representing a predefined population sample.

2. The method of embodiment 1, wherein the ophthalmic optical correction comprises use of an ophthalmic lens.

3. The method of embodiment 1, further comprising modifying an ophthalmic optical correction to include features of the ophthalmic optical correction based on the output value.

4. The method of embodiment 1, further comprising selecting an ophthalmic optical correction for use based on the output value.

5. The method of embodiment 1, wherein the set of indicia of image quality comprises an indication of resolution.

6. The method of embodiment 1, wherein the set of indicia of image quality comprises substantially only resolution information.

7. The method of embodiment 1, wherein the set of indicia of image quality comprises an indication of contrast.

8. The method of embodiment 1, wherein the set of indicia of image quality comprises substantially only contrast information.

9. The method of embodiment 1, wherein the set of indicia of image quality comprises resolution information and contrast information.

10. The method of embodiment 1, further comprising the step of repeating for a plurality of object distances.

11. The method of embodiment 1, wherein a series of objects of different sizes consists of a series of same letters of different sizes.

12. The method of embodiment 1, wherein the contact lens design on the solid substrate has been replaced by soft-contact lens conformed on a model cornea to simulate the behavior resulting from conformation of the lens on the human eye in presence of inherent aberrations.

13. The method of embodiment 1, wherein the contact lens design or a conformed soft lens is decentered with respect to optical axis to simulate performance of the lens in case of de-centration on the eye.

14. The method of embodiment 1, wherein multiple images are generated and scored for different pupil sizes.

15. The method of embodiment 1, wherein target objects are switched from characters in the clinic to natural scenes encountered in real life.

16. The method of embodiment 1, wherein target objects are varied not only in size but also contrast, described as variation in brightness between background and object of interest thereby simulating quantitative performance of the lens design in presence of difference contrast conditions.

17. The method of embodiment 1, wherein the system parameters are modified to simulate situations where both environmental and patient related parameters. For example, simulating night vision driving performance by using low contrast green and white targets with a large pupil setting.

Certain of the methods described herein may be performed by a suitably programmed processor, and may exist as instructions on a computer readable medium.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A method of predicting clinical performance of an ophthalmic optical correction by imaging on an optical bench having an adaptive optics system comprising a deformable mirror and a wavefront sensor a series of objects of different sizes which include letters of different sizes by each of a plurality of eye optical systems, each of the eye optical systems including the ophthalmic optical correction, a model eye, and a model eye pupil, the method comprising:

mounting the ophthalmic optical correction 500 in front of a model eye 510, adjusting a model eye pupil size 430 to represent an actual pupil size of a patient measuring the pupil size of the patient, recording an optical wavefront sans defocus, adjusting the deformable mirror 440 using the ocular wavefront sans defocus as an input 441 to represent the wavefront error of the patient eye, moving an object target 410 to beyond optical infinity and capturing an image 520 of the object target 410, moving the object target 410 to a vergence more positive by a known distance and capturing a second image 520 of the object target 410, continuing to move the object target 410 to a more positive vergence in steps by a known distance until a determined total vergence is reached while generating a series of letters having different letter sizes at each object target 410 distance, capturing an image 520 at all known distance step locations and all different letter sizes at each object target 410 distance, subjecting each captured image 520 at all known distance step locations to an algorithm to provide an output value representing a set of indicia of image quality of the optical design 500 at that vergence for the eye optical systems, comparing the output value at each vergence to a threshold to determine a just discernible object size for the given eye optical system at that vergence, and repeating the above method steps for any number of individual patients representing a predefined population sample.

2. The method of claim 1, wherein the ophthalmic optical correction comprises use of an ophthalmic lens.

3. The method of claim 1 further comprising modifying an ophthalmic optical correction to include features of the ophthalmic optical correction based on the output value.

4. The method of claim 1, further comprising selecting an ophthalmic optical correction for use based on the output value.

5. The method of claim 1, wherein the set of indicia of image quality comprises an indication of resolution.

6. The method of claim 1, wherein the set of indicia of image quality comprises substantially only resolution information.

7. The method of claim 1, wherein the set of indicia of image quality comprises an indication of contrast.

8. The method of claim 1, wherein the set of indicia of image quality comprises substantially only contrast information.

9. The method of claim 1, wherein the set of indicia of image quality comprises resolution information and contrast information.

10. The method of claim 1, wherein a series of objects of different sizes consists of a series of same letters of different sizes.

11. The method of claim 1, wherein the ophthalmic optical correction is a contact lens design on a solid substrate and wherein the contact lens design on a solid substrate is replaced by a soft-contact lens conformed on a model cornea to simulate the behavior resulting from conformation of the lens on the human eye in presence of inherent aberrations.

12. The method of claim 1, wherein the ophthalmic optical correction is a contact lens design or a conformed soft lens and wherein the contact lens design or conformed soft lens is decentered with respect to an optical axis to simulate performance of the lens in case of de-centration on the eye.

13. The method of claim 1, wherein multiple images are generated and scored for different pupil sizes.

14. The method of claim 1, wherein target objects are switched from characters in the clinic to natural scenes encountered in real life.

* * * * *